United States Patent [19]

Schneider

[11] Patent Number: 4,964,310

[45] Date of Patent: Oct. 23, 1990

[54] DISINTEGRATION TESTING DEVICE

[75] Inventor: Ortwin Schneider, Weiterstadt, Fed. Rep. of Germany

[73] Assignee: Erweka Apparatebau GmbH, Heusenstamm, Fed. Rep. of Germany

[21] Appl. No.: 311,057

[22] Filed: Feb. 15, 1989

[30] Foreign Application Priority Data

Feb. 15, 1988 [DE] Fed. Rep. of Germany ....... 3804688

[51] Int. Cl.$^5$ .......................................... G01N 19/00
[52] U.S. Cl. ..................................................... 73/866
[58] Field of Search ......................................... 73/866

[56] References Cited

U.S. PATENT DOCUMENTS 3,802,272  4/1974  Bischaft et al. ...................... 73/866
4,754,657  7/1988  Schneider ............................. 73/866

Primary Examiner—Tom Noland
Attorney, Agent, or Firm—Birch, Stewart, Kolasch & Birch

[57] ABSTRACT

A disintegration testing device for detecting the disintegration behavior of solid particles, in particular tablets, in a liquid, which comprises a supporting or holding device including a carrier which is movable in the upward and downward directions for supporting a vessel containing solid particles, a liquid bath into which the vessel can be submerged, a first lifting device which during normal operation moves the carrier and thus the vessel in the liquid in the upward and downward directions, and a second lifting device elevating the vessel from the liquid upon termination of one testing operation. The first lifting device includes a lifting arm which is driven by a motor through a drive shaft and a first roller disposed at a given distance spaced therefrom and supporting the supporting device. The second lifting device includes a second roller which is slidably movable out of the lifting arm and disposed at a greater radial distance from the driving shaft and supporting the supporting device upon it having been pushed in the outward direction for carrying out a larger stroke.

10 Claims, 5 Drawing Sheets

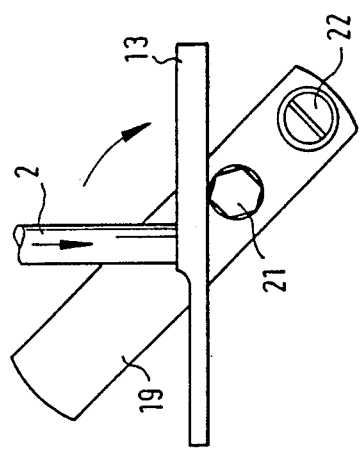
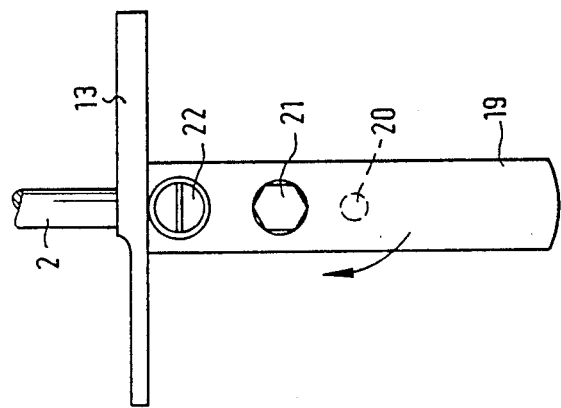
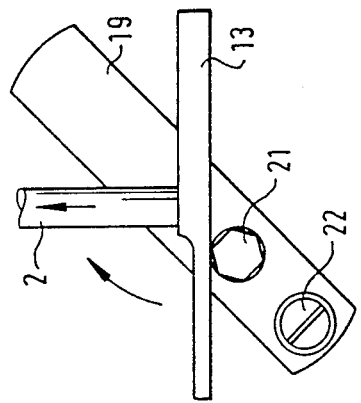
Fig. 4c
Fig. 4b
Fig. 4a

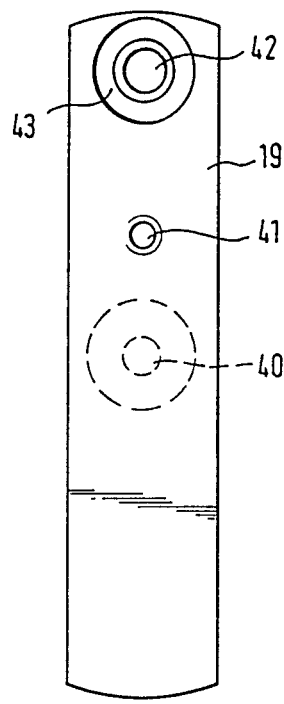
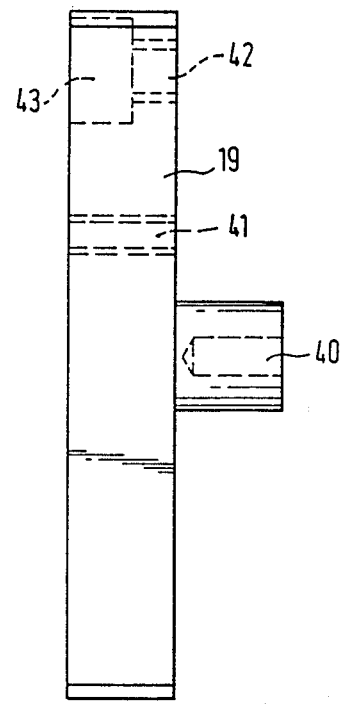
Fig. 5a          Fig. 5b
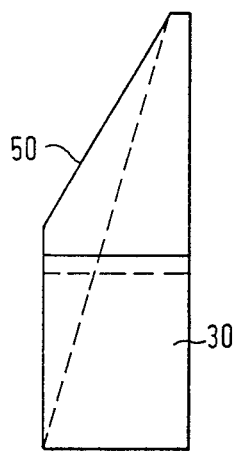
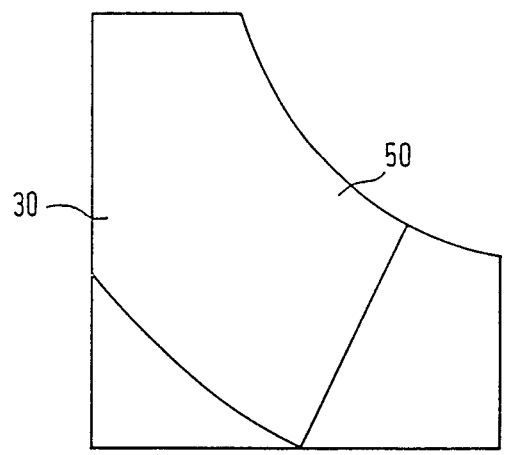
Fig. 6a          Fig. 6b

DISINTEGRATION TESTING DEVICE

BACKGROUND OF THE INVENTION

The present invention relates to a disintegration testing device for detecting the disintegration behavior or solid particles, in particular tablets, in liquids, the disintegration testing device comprising a supporting device having a carrier which is mounted for reciprocation in a vertical direction, for vessel for housing the solid particles, a liquid bath into which the vessel is submergeable, a first lifting device including a roller arranged at a lifting arm at a given distance from a motor driven driving shaft, which roller supports the carrier which moves the vessel in the upward and downward directions in the liquid upon a rotation of the lifting arm, and a second lifting device, which upon its activation, lifts the vessel out of the liquid bath.

Such a disintegration testing device has been available on the market for years. For carrying out a test it is necessary that a vessel is moved in upward and downward directions in a liquid bath for obtaining defined conditions during the disintegration process and for simulating the conditions to which the tablet is subjected upon disintegration within the body of the patient. For determining to what extent a tablet disintegrates within a time period of ten minutes, e.g., in the case of continuous movement in the liquid, it has up-to-now been the common practice to set the duration of operation of the driving motor to 10 minutes so that the motor stops after this period of time has elapsed. This time is controlled with more or less accuracy and the vessel is removed from the liquid manually. In the course of this action it cannot be avoided that the tablets unintentionally still remain in the liquid for some further time period prior to being removed, namely at such times when the laboratory assistant does not exactly establish the end of the test.

A disintegration testing device has already been known from the German utility model No. DE-GM 8615404.4, such device comprising a first lifting device which is driven by a motor and by means of which a supporting device is moved in the upward and downward directions, and a vessel containing the tablets and mounted on said supporting device and together therewith being moved in the upward and downward directions in the liquid. Such a known disintegration testing device comprises a second lifting device which, upon actuation, lifts the vessel out of the liquid. Upon lifting the motor is switched off and thus a reliable operation is achieved, as the vessel automatically is removed from the liquid at an exact point in time. The second lifting device, however, requires a comparatively large amount of expenditure.

SUMMARY OF THE INVENTION

It is, therefore, the main object of the present invention to create a disintegration testing device by means of which the vessel is automatically removable from the liquid and which, nevertheless, does not require a high degree of expenditure.

According to the present invention this problem is solved by a disintegration testing device wherein the second lifting device includes an activable second roller which is arranged at the lifting arm at a greater radial distance from the driving shaft than the first roller, which upon being activated, supports the carrier for lifting the vessel from the liquid.

The disintegration testing device according to the present invention provides the advantage that it requires only few moveable parts for the second lifting device and that it thus can easily be manufactured and works reliably.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIGS. 4a to 4c shows a second lifting device at different positions during the lifting of a vessel out of a liquid bath by means of a supporting device;

FIGS. 5a and 5b shows a lifting arm; and

FIGS. 6a and 6b show a wedge.

DETAILED DESCRIPTION OF THE INVENTION

Figure 1:
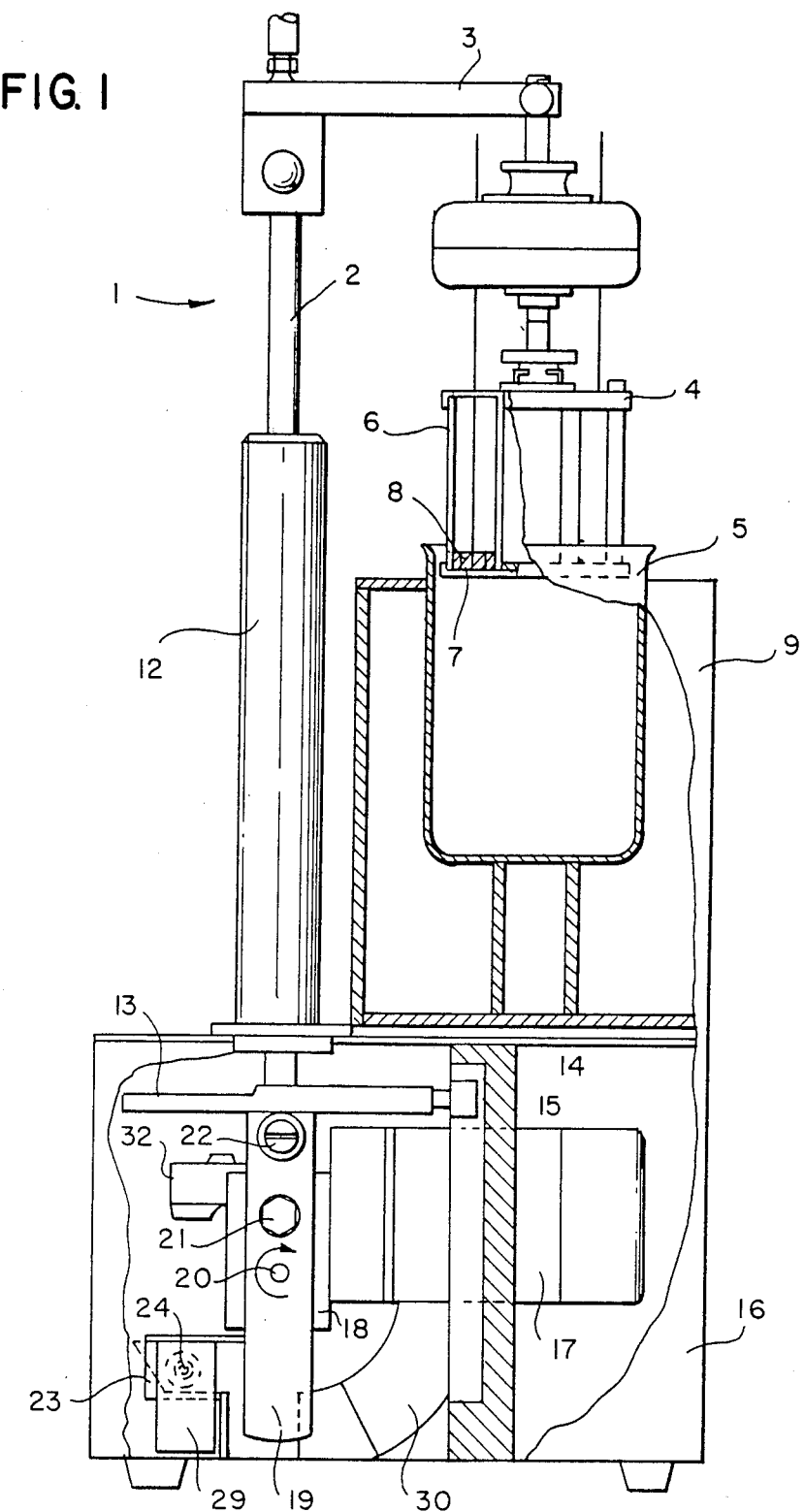
FIG. 1 shows the disintegration testing device in partially sectional first side view.
Figure 2:
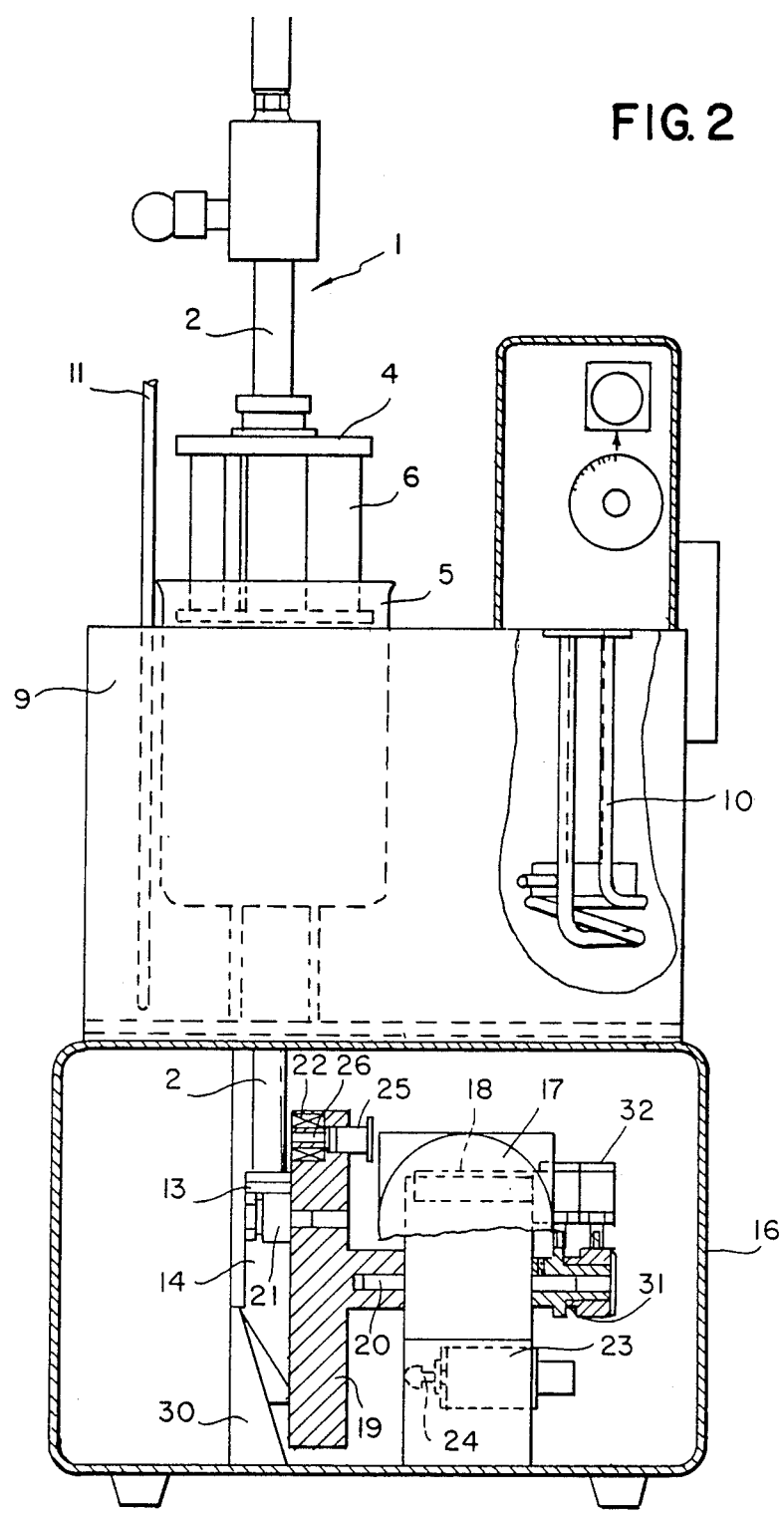
FIG. 2 shows the disintegration testing device in partially sectional second side view.

The disintegration testing device shown in FIGS. 1 and 2 comprises a supporting device 1 with a carrier 2 being movable in up- and downward directions, and a vessel 4 being suspended at the carrier via a gallow member 3. The vessel 4 contains tablets, the disintegration behaviour of which in a liquid contained in a bowl 5 is to be detected. Glass tubes 6 which are open at the bottom are disposed in the vessel 4 and stored on the screen-shaped bottom 7 of the vessel 4. In each of the glass tubes 6 is placed one tablet which is loaded with a disk 8.

The disintegration test is effected in such a manner that the vessel 4 is submerged into the liquid and is reciprocated therein in the vertical direction. Thereafter, the essential point to be detected is, the time in which the tablets disintegrate within the liquid. Therein, the liquid is maintained at a given temperature by immersing the bowl 5 into a liquid in a container 9. The heating of the liquid is effected by means of a heating device 10 which is controlled by a thermostat. An operating person may read the temperature from a thermometer 11. Upon termination of the test the vessel 4 again is lifted from the liquid.

The carrier 2 of the supporting device 1 is supported in a guide tube 12 allowing a reciprocating motion in the vertical direction and at its lower end is provided with a beam 13 which is arranged across the longitudinal direction of the carrier 2. For preventing the carrier 2 from distorting in the guide tube 12 a guide rail 14 is provided, having a recess which accommodates a running roller 15 which, in turn, is connected to the beam 13. The guide tube 12 and the guide rail 14 are stationary mounted at a socket member 16.

When the test is carried out the vessel 4 is reciprocated in the liquid between an upper and a lower position and at the end of the test the vessel 4 is lifted out of the liquid. For this purpose a first and a second lifting device are provided, see FIGS. 1 and 2.

The first lifting device serving for the upward and downward movement of the vessel 4 in the liquid comprises a lifting arm 19 driven by a motor 17 through a gearing 18, said arm being centrally connected to a driving shaft 20 driven by the gearing 18. At a first given distance from the driving shaft 20 a roller 21 on which the beam 13 is supported is rotatably fixed to the lifting arm 19. When the lifting arm 19 and the driving shaft 20 are rotated the roller 21 moves aroung the driving shaft 20 in a circular curve. As the beam 13 is supported on the roller 21, it is reciprocated in vertical direction and simultaneously the vessel 4 via the supporting device 1 is moved in up- and downward directions in the liquid.

Figure 3A:
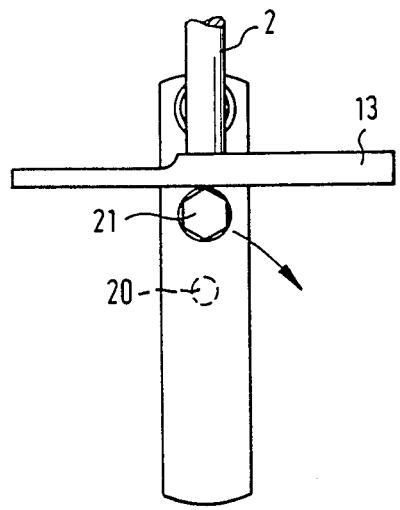
FIGS. 3a to 3d show a first lifting device at different positions during the up- and downward movements of a supporting device.
Figure 3B:
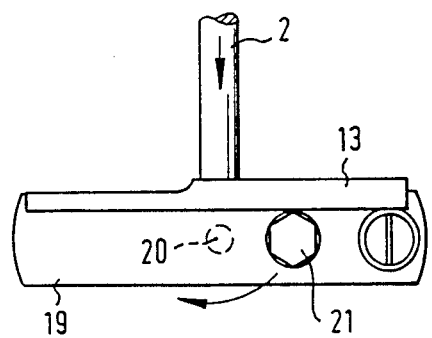
Figure 3C:
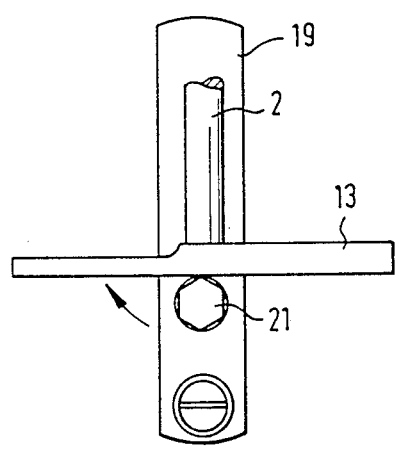
Figure 3D:
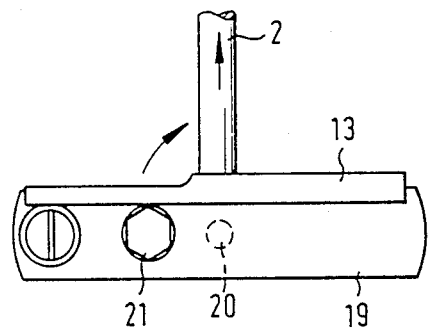

FIGS. 3a to 3d show the first lifting device in different positions during the rotation of the driving shaft 20. In the representation in FIG. 3a the beam 13 is in its uppermost position. In FIG. 3b the lifting arm 19 has been rotated clockwise by 90° and the beam 13 is in a central position. Upon a further rotation by 90° the beam 13 is in its lowest position, as can be seen from FIG. 3c. Upon a further rotation by 90° the beam 13 again resumes the central position, corresponding to that shown in FIG. 3b and being shown in FIG. 3d. Upon a further rotation by 90° a new cycle is started beginning at the position shown in FIG. 3a.

Simultaneously with the movement of the beam 13 according to FIG. 3 also the supporting device 1 and thus the vessel 4 are reciprocated in the vertical direction so that the tablets are reciprocated in the liquid.

The second lifting device for automatically lifting the vessel 4 out of the liquid is composed out of a further roller 22 mounted at the lifting arm 19 at a greater distance than the roller 21 from the driving shaft 20 and furthermore being made slidingly movable in the outward direction. The lifting is effected at the end of a test after a given period of time has elapsed and/or a given number of reciprocating motions, respectively, have been carried out in the liquid. Thereupon the second lifting device is actuated by means of an electromagnet 23 the armature 24 of which, in a suitable position with respect to the lifting arm 19, strikes a tappet 25 from the backside via a resilient tongue 29 and thereby strikes the support 26 or the roller 22 and slidingly moves the roller 22 out of the lifting arm 19 to the front. The sliding outward movement is effected in particular when upon a rotation of the lifting arm 19 the roller 22 is positioned below the roller 21, as can be seen, e.g., from the position shown in FIG. 3b or FIG. 3d.

The movement of the roller 22 back into the lifting arm 19 is effected by means of a wedge 30 arranged opposite to the electromagnet 23 in the lower region of the socket member 16. During the rotation of the lifting arm 19 the outwardly moved roller 22 strikes the wedge 30 so that the roller is moved back into the lifting arm 19 during its further rotation by said wedge 30.

In the representation shown in FIG. 4a the beam 13 is supported on the roller 21, as is the case during the normal vertical reciprocating movement of the vessel 4 in the liquid during the rotation of the lifting arm 19 and in this position the electromagnet 23 is activated so that its armature 24 strikes the tappet 25 from the backside via the resilient tongue 29 and pushes the roller 22 out of the lifting arm 19. After the horizontal position of the lifting arm 19 corresponds to the view of FIG. 3d then the roller 22 serves for further supporting the beam 13 so that the stroke thereof increases. In the position shown in FIG. 4b the beam 13 has reached its uppermost position and in this position the vessel 4 is lifted out of the liquid via the supporting device 1. In this position the motor 17 is stopped and the test is terminated.

At a renewed start of the motor 17 the lifting arm 19 is rotated again and upon the lifting arm 19 having left the position shown in FIG. 3b, the roller 21 again takes over the support of the beam 13. In the position shown in FIG. 4c the roller 22 moved outwardly again impinges on the wedge 30, so that it is moved back into the lifting arm 19 during the further rotation thereof and a motion corresponding to FIGS. 3a to 3d is repeated, i.e., the vessel 4 is reciprocated in the vertical direction in the liquid until the electromagnet is activated again and the roller 22 via the supporting device 1 effects the removal of the vessel 4 from the liquid.

The selection of the electromagnet 23 and the subsequent stopping of the motor 17 in the uppermost position of the beam 13 is effected by switches 32 which are controlled by cam disks 31 arranged at the backward end of the driving shaft 20.

The lifting arm 19 shown in FIGS. 5a and 5b has a bore 40 for the driving shaft 20 as well as a thread 41 for fixing the roller 21 of the first lifting device. Furthermore the lifting arm 19 has a bore 42 for the support of the roller 22 by the bearing 26 and for guiding the tappet 25 as well as a recess 43 for receiving the roller 22 in the retracted position.

FIGS. 6a and 6b show the wedge 30 in a side view and a top view, respectively. The wedge 30 is fixed to the bottom of the socket member 16 and has a support area 50 onto which the roller 22 impinges when being moved out of the lifting arm 19 during the further rotation thereof. The support area 50 is inclined with respect to the circumferential direction and pushes the roller 22, which has been moved out of the lifting arm 19 upon a further rotation thereof, back into its recess 43, presuming that only one reciprocating motion of the supporting device 1 in the vertical direction is to be carried out.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed :

1. A disintegration testing device for detecting the disintegration behavior of solid particles in liquids, which comprises
    a supporting device having a carrier which is mounted for reciprocating in a vertical direction, said carrier supporting a vessel which contains the solid particles,
    a liquid bath into which the vessel is submergible,
    a first lifting device including a roller which is arranged at a lifting arm at a given distance from a drive shaft driven by a motor, said roller supporting the carrier which moves the vessel in the upward and downward directions in the liquid upon a rotation of the lifting arm, and
    a second lifting device which, upon its activation, lifts the vessel out of the liquid bath, said second lifting device including an activable second roller which is arranged at the lifting arm at a greater radial distance from the driving shaft than the first roller and upon its activation supports the carrier for lifting the vessel out of the liquid.

2. The disintegration testing device as defined in claim 1, wherein the second roller is arranged at the lifting arm in the same radial direction as the first roller.

3. The disintegration testing device as defined in claim 1, wherein the activation of the second roller is effected by said roller being slidingly moved out of the lifting arm in the vertical direction.

4. The distintegration testing device as defined in claim 3, wherein the sliding, outward motion of the second roller is effected by means of an electromagnet.

5. The disintegration testing device as defined in claim 4, wherein the armature of the electromagnet strikes a bearing of the second roller, disposed in the lifting arm from a rearside thereof.

6. The disintegration testing device as defined in claim 5, wherein the armature strikes the bearing via a tappet.

7. The disintegration testing device as defined in claim 4, wherein the selection of the electromagnet is effected by a switch which is actuated by a cam disk.

8. The disintegration testing device as defined in claim 3, wherein the sliding backward movement of the second roller into the lifting arm is effected by means of a wedge, on an inclined surface of which the second roller impinges upon rotation of the lifting arm.

9. The disintegration testing device as defined in claim 8, wherein the wedge and the magnet are arranged below the drive shaft.

10. The disintegration testing device as defined in claim 1, wherein a switching off of the motor is effected via a cam disk.

* * * * *